"(12) United States Patent" (10) Patent No.: US 8,338,588 B2
Hunt (45) Date of Patent: Dec. 25, 2012

(54) METHANESULFONATE SALTS OF ABIRATERONE-3-ESTERS AND RECOVERY OF SALTS OF ABIRATER ONE-3-ESTERS FROM SOLUTION IN METHYL TERT-BUTYL ETHER

(75) Inventor: Neil John Hunt, Manchester (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 13/317,997

(22) Filed: Nov. 2, 2011

(65) Prior Publication Data

US 2012/0053340 A1 Mar. 1, 2012

Related U.S. Application Data

(60) Continuation of application No. 12/656,581, filed on Feb. 4, 2010, now Pat. No. 8,076,474, which is a division of application No. 11/660,869, filed as application No. PCT/GB2005/003282 on Aug. 23, 2005, now Pat. No. 7,700,766.

(60) Provisional application No. 60/603,559, filed on Aug. 24, 2004.

(30) Foreign Application Priority Data

Aug. 24, 2004 (GB) .................................. 0418900.7

(51) Int. Cl.
C07J 43/00 (2006.01)
(52) U.S. Cl. ......................................................... 540/95
(58) Field of Classification Search ...................... 540/95
See application file for complete search history.

(56) References Cited

U.S. PATENT DOCUMENTS

| 5,618,807 A | 4/1997 | Barrie et al. .................. 514/176 |
| 8,076,474 B2 * | 12/2011 | Hunt ............................... 540/65 |

FOREIGN PATENT DOCUMENTS

| WO | WO 93/20097 | 10/1993 |
| WO | WO 95/09178 A | 4/1995 |

OTHER PUBLICATIONS

Potter, et al II, "Novel Steroidal, etc.," *J. Med. Chem.*, 38, pp. 2463-2471 (1995).
Haidar, et al, "C16 and C17, etc.," *Arch. Pharm. Pharm. Med. Chem.*, 11, pp. 526-534 (2002).
Orsini, et al, "Influence of the, etc.," *J of Organometallic Chemistry*, 367, pp. 375-382 (1989).
Anne, et al, "Formal Hydride, etc.," *JACS*, 115 (22), pp. 10224-10230 (1993).
Deutsch, et al, "Noncoordinating Buffers, etc.," *J Org. Chem.*, 38(6), pp. 1123-1126 (1973).
Hopkins, et al, "Basicities of, etc.", *JACS*, 106 (16), pp. 4341-4348 (1984).
Brown, et al., "Preparation and Reactions, etc.," *JACS*, 88 (5), pp. 986-992 (1966).
Specification of co-pending U.S. Appl. No. 11/660,869, filed Feb. 22, 2007 (26 pgs).
Potter, G. A., et al; "A convenient, large-scale synthesis of abiraterone acetate '3.beta.-acetoxy-17-(3-pyridyl)androsta-5,16-diene!, a potential new drug for the treatment of prostate cancer"; *Organic Preparations and Procedures Int'l*; vol. 29(1); pp. 123-128; (1997) XP008056111.

* cited by examiner

*Primary Examiner* — Patricia Morris
(74) *Attorney, Agent, or Firm* — Nixon & Vanderhye

(57) ABSTRACT

A salt of a compound of formula (I) may be made with methanesulfonic acid. The salt and salts with other acids may be prepared by recovering from methyl tert-butyl ether (MTBE).

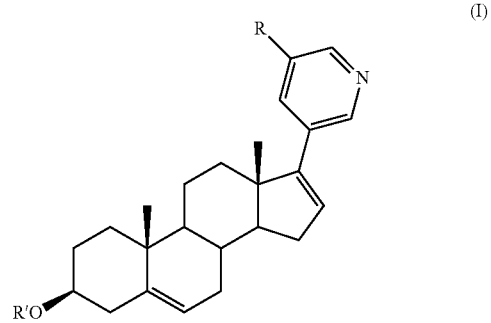

6 Claims, No Drawings

METHANESULFONATE SALTS OF ABIRATERONE-3-ESTERS AND RECOVERY OF SALTS OF ABIRATER ONE-3-ESTERS FROM SOLUTION IN METHYL TERT-BUTYL ETHER

This application is a continuation of application Ser. No. 12/656,581 filed Feb. 4, 2010, U.S. Pat. No. 8,076,474, which is a divisional of application Ser. No. 11/660,869 filed Mar. 28, 2007, U.S. Pat. No. 7,700,766, which is a 371 of PCT/GB2005/003282 filed Aug. 23, 2005, which claims priority to British Application No. 0418900.7 filed Aug. 24, 2004 and which claims benefit of Provisional Application No. 60/603,559 filed Aug. 24, 2004, entire contents of each of which are hereby incorporated by reference.

This invention relates to novel salt forms of the esters of the compound abiraterone, or a derivative thereof, and to a process for the preparation of the compound abiraterone, or a salt or derivative thereof.

Abiraterone acetate of formula:

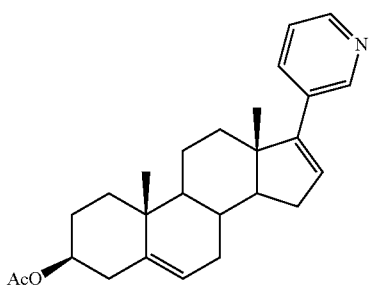

is a potent selective, orally active inhibitor of the key enzyme in testosterone synthesis, 17α-hydroxylase-C17,20-lyase, also known as steroid 17α-monooxygenase inhibitor or Human Cytochrome $P450_{17\alpha}$. Suppression of testosterone synthesis has been demonstrated with abiraterone acetate in patients with prostate cancer.

The compound was first disclosed in WO-A-93/20097, with a further synthetic method to the compound in WO-A-95/09178 (both British Technology Group Limited). In particular, WO-A-95/09178 discloses the synthesis of a compound of formula:

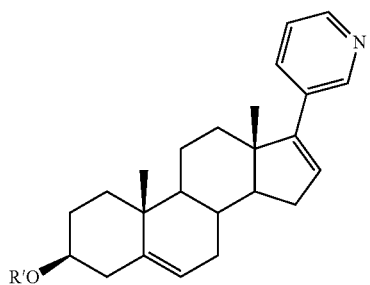

where the 3β substituent R' is hydrogen or a lower acyl group having 2 to 4 carbon atoms. One of the methods disclosed makes this from the corresponding ketone via the steroidal enol triflate (trifluoromethylsulfonate):

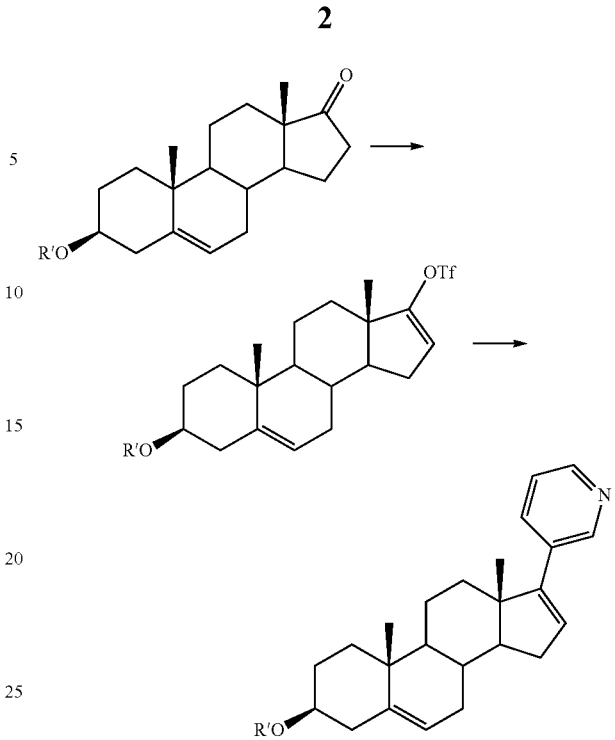

The base used in the reported route, 2,6-di-tert-butyl-4-methylpyridine (DTBMP), is expensive. The present inventors have moreover observed a problem with this process in that, when R' is a lower acyl group, elimination of the acid occurs, giving an undesirable by product of formula:

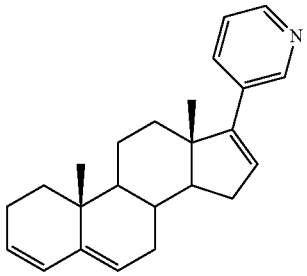

The by-product cannot be removed by recrystallisation at either step. Therefore column chromatography is required at both steps WO-A-95/09178 suggests replacing the triflate with a corresponding vinyl iodide intermediate, and uses this to make compounds by reacting this with a (3-pyridyl)-substituted borane of formula:

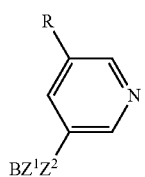

wherein R represents a hydrogen atom or an alkyl group of 1-4 carbon atoms and $Z^1$ and $Z^2$ independently represent hydroxy or alkoxy or alkyl of 1-3 carbon atoms each or $Z^1$ and $Z^2$ together represent an alkylenedioxy group of 2 or 3 carbon atoms.

However, column chromatography is required for this process also.

We have now developed an improved route in which a salt of the desired compound is recovered from a suitable solvent. The undesirable by-product remains in solution. This means that the purification process is simplified, as expensive and time-consuming column chromatography steps can be eliminated.

Accordingly the present invention comprises the salt of a compound of formula (I):

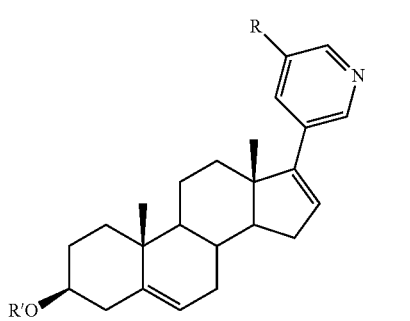
(I)

where R' represents a lower acyl group having 2 to 4 carbon atoms and R represents a hydrogen atom or an alkyl group of 1-4 carbon atoms;

with methanesulfonic acid.

The salt may be recovered from a solution of the free base in any suitable solvent, or mixture of solvents, by treating the solution with methanesulfonic acid. Suitable solvents include esters and ethers. Esters which may be used include esters withy acetic acid, such as methyl acetate, ethyl acetate and isopropyl acetate. Ethers which may be used include diethyl ether, diisopropyl ether and especially methyl tert-butyl ether (MTBE), which gave a particularly good recovery of the salt.

The inventors have found moreover that other salts of the compound may be recovered in acceptable amounts from MTBE. The present invention also includes a process for the preparation of a compound of formula (I):

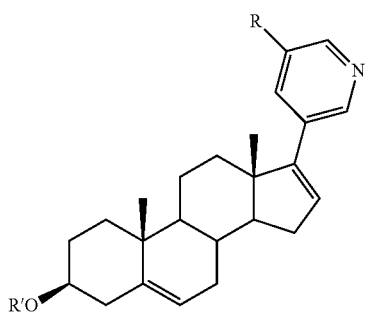
(I)

where R' represents hydrogen or a lower acyl group having 2 to 4 carbon atoms and R represents a hydrogen atom or an alkyl group of 1-4 carbon atoms;

or a pharmaceutically acceptable salt thereof;

including the step of recovering a salt of the compound, where R' represents a lower acyl group having 2 to 4 carbon atoms and R is as defined above, from methyl tert-butyl ether (MTBE).

Preferably the acid is hydrochloric, sulfuric or toluoyltartaric acid, or in particular methanesulfonic acid.

Using the present invention, a method for the preparation of the compound of formula (I) is possible which requires no chromatographic purification at any stage of the synthesis. The invention is particularly applicable when the salt of the compound of formula (I) is recovered from a solution in MTBE comprising a mixture of the compound of formula (I) and a compound of formula (IV):

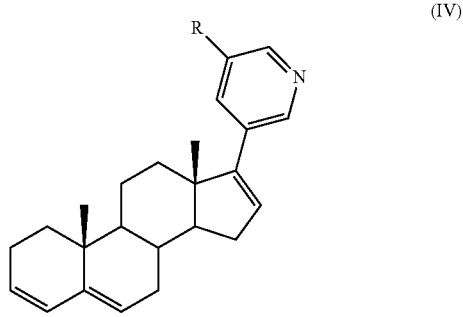
(IV)

wherein R is as defined above.

Preferably R' represents a lower acyloxy group, especially acetyl. Preferably R represents a hydrogen atom. Most preferably R' represents acetyl and R represents a hydrogen atom, the compound of formula (I) being abiraterone acetate.

The compound of formula (I) may be made by a process including a triflating step by which a ketone of formula (II) is converted into a triflate of formula (III):

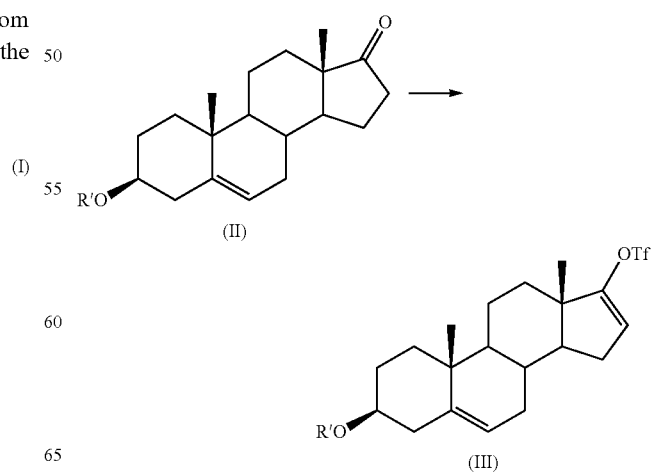

wherein R' and R are as defined above, or a protected derivative thereof;

the triflating step being conducted in the presence of a base comprising a tertiary or heterocyclic amine such that the $pK_a$ of the conjugate acid at 25° C. is within the range 5.21 to 12.

Using this improved route, the production of the undesirable by-product is kept down to acceptable levels. As this does not use the expensive reagent DTBMP, the route is made commercially more attractive still.

Preferred bases include those set out in Table 1:

TABLE 1

Preferred bases

| Base | $pK_a$ of conjugate acid at 25° C. |
|---|---|
| pyridine | 5.21 |
| 2,6-lutidine | 6.75 |
| N-methylmorpholine | 7.38 |
| 1,4-diazabicyclo[2.2.2]octane (DABCO) | 8.82 |
| trimethylamine | 9.81 |
| triethylamine | 10.6 |
| N,N-diisopropylethylamine (DIPEA) | 11 |
| quinuclidine | 11.0 |
| 1,8-diazabicyclo[5.4.0]undec-7-ene (DBU) | 12 |

Preferably the $pK_a$ of the conjugate acid at 25° C. is within the range 6.75 to 10.6. Most preferably the base is 2,6-lutidine or triethylamine.

Preferably the triflating step is carried out in a solvent comprising an chlorinated organic solvent or an organic ester. Suitable organic esters include ethyl acetate. Preferably the solvent is a chlorinated organic solvent such as chloroform, and in particular dichloromethane or 1,2-dichloroethane In the case where R' represents hydrogen, the protecting group could be any suitable group for protecting alcohols, as discussed in "Protective groups in organic synthesis" $3^{rd}$ Ed, Theodora W Greene and Peter G. Wuts, published by John Wiley, ISBN 0-471-16019-9. For example, it might be protected as a benzyl, methoxymethyl (MOM) or silyl ether.

In the case where R' represents a lower acyloxy group, no further protection would normally be necessary.

The preferred triflating agent is triflic anhydride ($Tf_2O$). To minimize decomposition of the product, preferably the base is added to the reaction mixture shortly after the triflic anhydride, say fifteen minutes or less. The reaction mixture is preferably quenched within an hour after the addition of the base, again to minimize decomposition of the product.

We have observed that the use of large excesses of base lead to poor conversion of the ketone of formula (II) into the triflate of formula (III), and that use of large excesses of triflic anhydride can lead to rapid decomposition of the product. For optimum conversion of the ketone of formula (II) into the triflate, the number of equivalents of triflic anhydride is preferably not lower than the number of equivalents of base. We have also observed that reducing the amount of base to sub-stoichiometric levels did not affect the conversion.

Thus preferably the triflating step is performed using between 1.0 and 1.5 equivalents, more preferably between 1.1 and 1.4 equivalents, of triflic anhydride relative to the ketone of formula (II); and between 0.75 and 1.5 equivalents of base, more preferably between 0.8 and 1.4 equivalents, relative to the ketone of formula (II), wherein the number of equivalents of triflic anhydride is greater than or equal to the number of equivalents of base. More preferably, the number of equivalents of triflic anhydride is greater than the number of equivalents of base.

The preparation of the ketone of formula (II), and the conversion of the triflate of formula (III) to a compound of formula (I), are by known methods. Thus, the triflate of formula (III), or a protected derivative thereof, may be reacted with a (3-pyridyl)-substituted borane of formula:

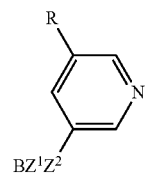

wherein R represents a hydrogen atom or an alkyl group of 1-4 carbon atoms and $Z^1$ and $Z^2$ independently represent hydroxy or alkoxy or alkyl of 1-3 carbon atoms each or $Z^1$ and $Z^2$ together represent an alkylenedioxy group of 2 or 3 carbon atoms;

in the presence of a palladium complex and a polar solvent, using the Suzuki coupling. This is disclosed in WO-A-93/20097.

The salts of the compounds of formula (I) may if necessary be converted to the free base form and thereafter to such other conventional pharmaceutically acceptable acid addition salts as acetates, citrates, lactates, alkanesulfonates (e.g. methanesulfonate), and optionally substituted tartrates as may seem appropriate.

In this specification the term "alkyl" includes both straight and branched chain. An analogous convention applies to other generic terms such as "alkoxy", "acyl" and "alkylenedioxy".

It is to be understood that all the ketone of formula (II) disclosed may exhibit the phenomenon of tautomerism and that the formulae shown in this specification represent only one of the possible tautomeric forms. It is to be understood therefore that the invention is not limited merely to any one tautomeric form which is illustrated. For example, the ketone of formula (II) may also exist as an enol of formula (IIA)

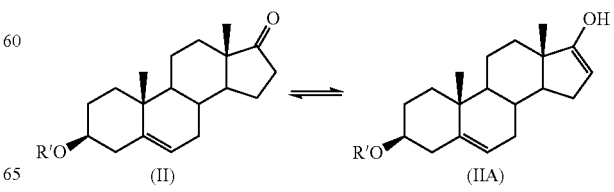

The invention is illustrated by the following Examples.

EXAMPLE 1

Salt Screen for the Purification of Abiraterone Acetate 1

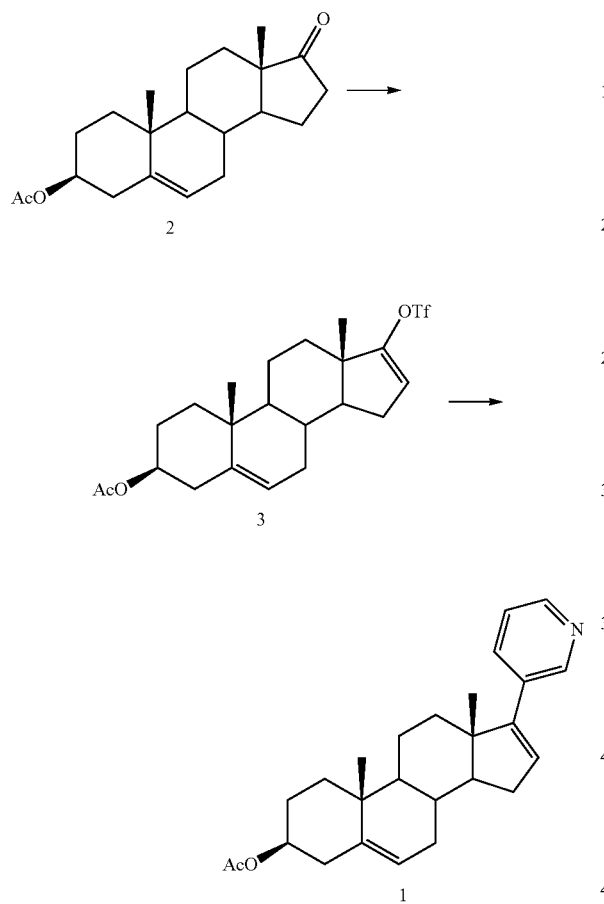

Following the synthesis of abiraterone acetate 1 from the corresponding ketone 2, in order to separate the abiraterone acetate 1 from the ketone 2, a solution of the mixture was treated with an acid to form a salt of 1 which would precipitate out of solution leaving the ketone 2 in solution. A matrix of acids and solvents was set up to find the ideal conditions for recovery and purity of the isolated salt.

The general procedure for the salt screen was to add the acid (0.27 mmol.) to a solution of the mixture of 1 and 2 (0.26 mmol) in the solvent (10 vol.). The reaction was left for 1 hour at which point any solids were filtered. The remaining reaction were left for a further 47 hours and were inspected. Any solids collected were analysed by $^1$H NMR. See Table 2.

TABLE 2

Salt screen for the purification of abiraterone acetate 1.

| Solvent | Acid | | | |
|---|---|---|---|---|
| | Tartaric | Acetic | Malic | Methane sulfonic |
| Ethyl acetate | 1 hr - x acid not in solution 48 hr - x | 1 hr - x 48 hr - x | 1 hr - ✓ fine suspension. 48 hr - ✓ unchanged over time | 1 hr - ✓ thick precipitate, filtered at this stage (27 mg) |
| MTBE | 1 hr - x acid not in solution 48 hr - ✓ fine crystals | 1 hr - ✓ fine suspension 48 hr - ✓ fine suspension | 1 hr - ✓ sticky solid 48 hr - ✓ no change | 1 hr - ✓ thick precipitate, filtered at this stage (52 mg) |

✓ - solid formed.
x - no solid formed.

The reaction with methanesulfonic acid in both ethyl acetate and MTBE furnished the methanesulfonate salt in high purity with no detectable presence, by $^1$H NMR, of 2 after filtration. On a larger scale (24.4 mmol) the salt was recovered in 64% yield at 87.7% yield. The resulting salt was recrystallised from isopropyl alcohol giving a 41% yield at 96.4% purity by peak area.

This material was subjected to a range of alternative recrystallisation conditions, in attempt to increase the purity to >98% (see Table 3).

TABLE 3

Alternative recrystallisation methods

| | Conditions | Purity (%) | Recovery (%) |
|---|---|---|---|
| 1 | Recrystallised from minimum volume of boiling ethanol (12 vol.). | 98.8 | 32 |
| 2 | Slurried in boiling ethyl acetate (5 vol.) and minimum volume of methanol added (5 vol.) for dissolution | 99.3 | 35 |
| 3 | Slurried in boiling acetone (35 vol.) | 96.8 | 30 |
| 4 | Dissolved in DCM (5 vol.) and ethyl acetate added until crystallisation occurs | 97.7 | 82 |

The free base can be recovered quantitatively from the salt by treatment of a solution of the salt in DCM with saturated aqueous NaHCO$_3$. There is no degradation in purity during this treatment.

EXAMPLE 2

Large Scale Synthesis of Abiraterone Acetate 1

Synthesis was conducted as in Scheme 1.

Scheme 1

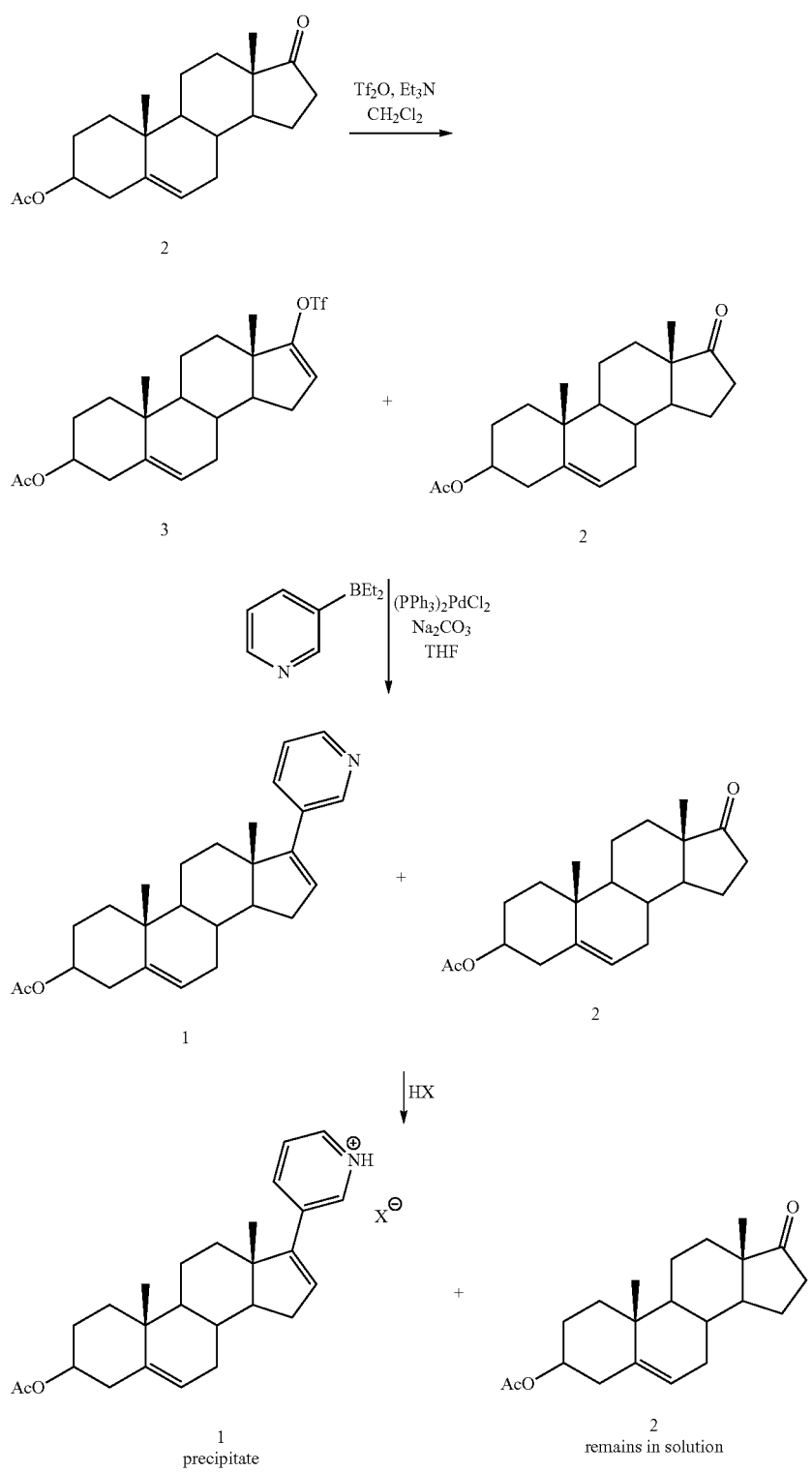

The optimised route was performed on a 10 g scale. The formation of the triflate yielded the crude product in an 80% yield (11.20 g) with a product to starting material ratio of 3:1. The Suzuki reaction was performed on the crude product using a catalyst loading of 0.5 mol %. The product of the Suzuki reaction was isolated in a quantitative crude yield (9.54 g). The ratio of product to ketone 2 was 3:1. This yield was also concurrent with the smaller scale reactions.

The abiraterone acetate was purified by formation and crystallisation of its methanesulfonate salt from EtOAc/

MTBE. The salt was isolated in a 64% yield (7.65 g) and at 87.7% purity. This was subsequently recrystallised from a minimum volume of boiling isopropyl alcohol (95 cm³) to yield the salt in 63% recovery (4.85 g) and at 96.4% purity.

Experimental

Triflate Formation 3

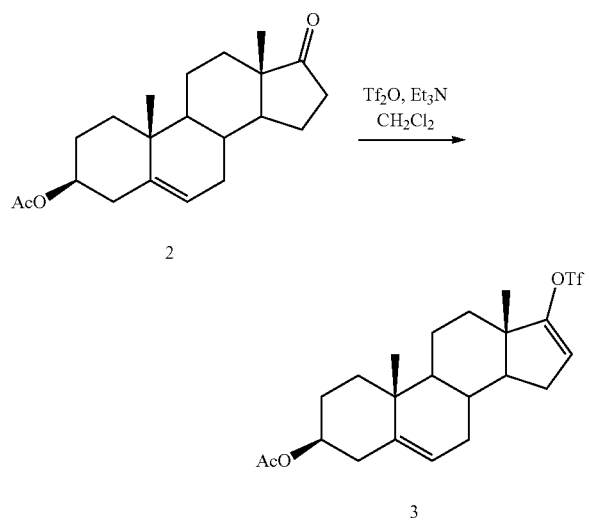

To a stirred solution of dehydroepiandrosterone acetate 2 (10 g, 30.3 mmol.) in CH₂Cl₂ (100 cm³, 10 vol.) was added Tf₂O (5.60 cm³, 33.3 mmol, 1.1 eq.) and the reaction was stirred at room temperature for five minutes. A solution of triethylamine (4.22 cm³, 30.3 mmol, 1.0 eq.) in CH₂Cl₂ (100 cm³, 10 vol.) was added over 25 minutes. The resulting purple solution was stirred at room temperature for 3.5 hours. The reaction was quenched by addition of water (150 cm³, 15 vol.) and the layers separated. The aqueous layer was extracted with CH₂Cl₂ (75 cm³, 7.5 vol.) and the organic layers were combined. The organic fraction was washed with 2N HCl (75 cm³, 7.5 vol.) and brine (75 cm³, 7.5 vol.). The organic layer was treated with MgSO₄ and activated charcoal (7.0 g, 0.7 wt eq.) for 10 minutes. The suspension was filtered through a pad of Celite™ and the filtrate was concentrated under reduced pressure to yield a brown oil, 11.20 g (80% crude yield). ¹H NMR (CDCl₃) showed the ratio of product 3 to starting material 2 to be 3:1

Abiraterone Acetate 1

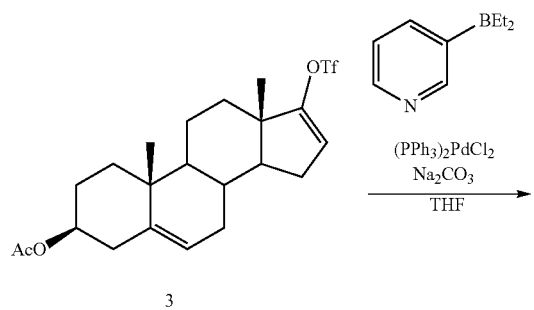

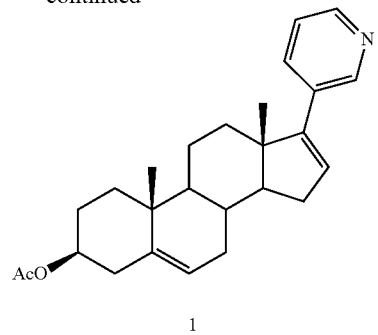

Pd(PPh₃)₂Cl₂ (97 mg, 0.14 mmol, 0.006 eq.), diethyl (3-pyridyl)borane (6.11 g, 41.5 mmol, 1.7 eq.) and 2M Na₂CO₃ (aq) (55 cm³, 111 mmol, 4.5 eq.) were added consecutively to a stirred solution of the mixture of triflate 3 and ketone 2 (11.20 g, 27.7 mmol assuming all substrate is triflate 3) in THF (130 cm³, 10 vol.). The reaction was heated to 80° C. and stirred at this temperature for 5 hours. The reaction was cooled to room temperature and partitioned between ethyl acetate (130 cm³, 11 vol.) and water (130 cm³, 11 vol.). The layers were separated and the aqueous layer extracted with ethyl acetate (65 cm³, 5.5 vol.). The combined organic layers were dried over MgSO₄ and concentrated under reduced pressure to yield a brown oil. This oil was stirred in MeOH (35 cm³, 3 vol.) and was gently warmed with a hot air gun. A white solid (unreacted diethyl (3-pyridyl)borane) precipitated and was filtered. The filtrate was concentrated under reduced pressure to yield a brown oil (9.54 g, 100% yield). ¹H NMR showed that this material was a 3:1 mixture of abiraterone acetate 1 and ketone 2.

Salt Formation

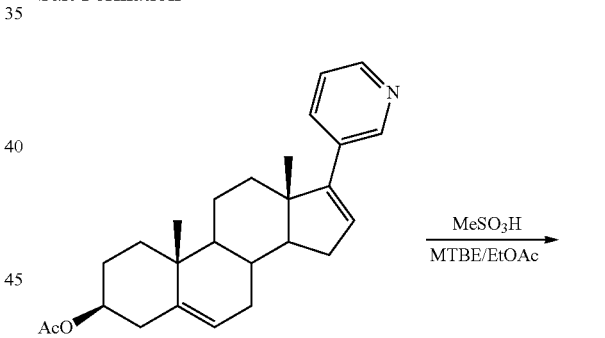

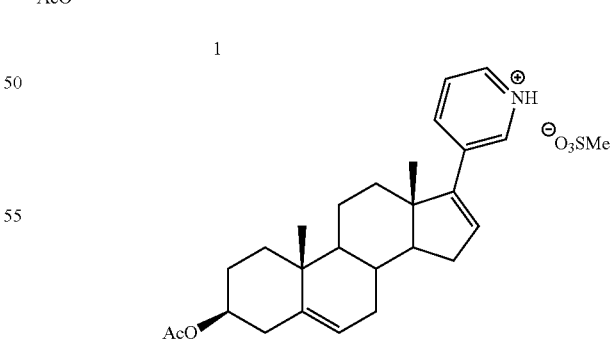

Methanesulfonic acid (1.86 cm³, 25.6 mmol, 1.05 eq.) was added to a stirred solution of the mixture of 1 and 2 (9.54 g, 24.4 mmol assuming entirely steroid 1) in a mixture of MTBE (50 cm³, 5 vol.) and ethyl acetate (50 cm³, 5 vol.). The resulting thick suspension was filtered and the cake washed with MTBE (10 cm³, 1 vol.). The cake was dried in air to yield a tan solid (7.65 g, 64% yield based on all starting material being steroid 1, 87.7% purity by HPLC). The salt was recrystallised from boiling isopropyl alcohol (95 cm³) to yield a tan solid (4.85 g, 41% yield, 96.4% purity by HPLC).

EXAMPLE 3

Formation of Salts of Abiraterone Acetate

The principle of purification via salt formation is shown in Scheme 2.

Scheme 2: Purification of abiraterone acetate via salt formation

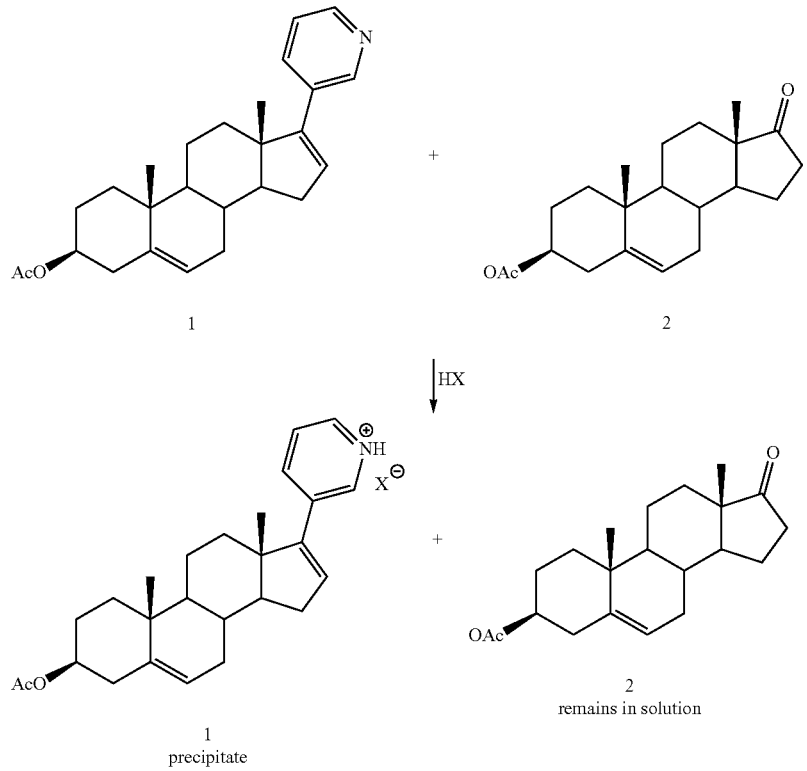

A Screen of Alternative Solvents

A screen was performed of ether and ester solvents which the methanesulfonate salt of abiraterone acetate could be crystallized from.

The acid was added to a solution of crude abiraterone acetate (approx 70:30 abiraterone acetate to DHEA) in 8 volumes of the reaction solvent. The mixture was stirred for one hour at room temperature and any reaction showing the formation of a filterable solid was filtered, and a ¹H NMR of the solid taken. See Table 4.

TABLE 4

| Alternative solvents | | | | | |
|---|---|---|---|---|---|
| Et₂O | ⁱPr₂O | MTBE | MeOAc | EtOAc | ⁱPrOAc |
| 1 hr-X 16 hr-✓ (34% recovery) | 1 hr-✓ (37% recovery) | 1 hr-✓ (43% recovery) | 1 hr-✓ (11% recovery) | 1 hr-✓ (22% recovery) | 1 hr-✓ (31% recovery) |

✓ - Filterable solid formed which contains negligible DHEA.
X - No purification detected.

The methanesulfonate salt crystallised readily from all the ethers and esters tested but a better yield was recovered as the lipophilicity of the solvent was increased. When crystallisation did occur, abiraterone acetate was purified to a level comparable with that seen from the ethyl acetate/MTBE biphasic mixture.

A Screen of Alternative Acids

A wider range of acids to was screened. Some inorganic acids (hydrogen chloride and sulfuric acid) were tested as well as a more lipophilic acid, toluoyltartaric acid.

The acid (1.05 eq.) was added to a solution of crude abiraterone acetate (250 mg, 70:30 abiraterone acetate to DHEA) in 10 volumes of the solvent. The reaction was stirred at room temperature for an hour and any solid formed was filtered and checked by ¹H NMR. See Table 5.

TABLE 5

| Alternative acids | | | |
|---|---|---|---|
| | MTBE | EtOAc | MeOH |
| HCl (2M in Et₂O) | ✓ (48% recovery) | ✓ (30% recovery) | X |
| H₂SO₄ (5M in H₂O) | ✓ (48% recovery) | X (sticky oil) | X |
| Ditoluoyltartaric acid | ✓ (40% recovery) | ✓ (20% recovery) | X (small quantity of sticky solid after 16 hours) |

✓ crystallisation occurred after 1 hour (unless stated) and ketone removed.
X no filterable solid formed. No crystallisation unless stated.

Formation of the chloride and ditoluoyltartrate from MTBE and EtOAc and the sulfate from MTBE were reasonable alternatives to the methanesulfonate salt. All the isolated salts purified the abiraterone acetate to the same degree as that gained from the formation of the methanesulfonate.

Solubility and Dissolution Studies

Samples of abiraterone acetate and its mesylate salt were investigated for their solubility in water and the rate of dissolution in water.

Abiraterone Acetate Free-Base

Appearance 1 Large, dark-brown, amorphous 'glass-like', aggregates (pre-pestle & mortar grinding)

Appearance 2 Pale tan-coloured powder (post-pestle & mortar grinding)

Solubility @ 20° C., 0 mg/mL (Insoluble)

Dissolution Rate @ 20° C. No discernable dissolution of compound observed, as evidenced by there being no observable peaks on the base-lines of the HPLC chromatograms.

Abiraterone Acetate, Mesylate Salt

Appearance 1 Large, mid-brown, broken-sheet, plate aggregates (pre-pestle & mortar grinding)

Appearance 2 Pale tan-coloured powder (post-pestle & mortar grinding)

Solubility @ 20° C. 0.03-0.05 mg/mL, nominally 0.04 mg/mL (Practically Insoluble)

Equivalent to 30-50 µg/mL, nominally 40 µg/mL

Dissolution Rate @ 20° C. Maximal solubility achieved within 60 minutes, although it was not possible to quantify earlier time-point samples due to the Limit of Detection (LOD)/Limit of Quantification (LOQ) limitations of the current HPLC method.

It can be seen from these results that neither the free base nor the mesylate salt is particularly soluble in water.

EXAMPLE 4

Preliminary Investigations into Reaction Steps

Step 1—Formation of the Triflate

The formation of the triflate may also give the eliminated impurity 4, which is very difficult to remove by crystallisation:

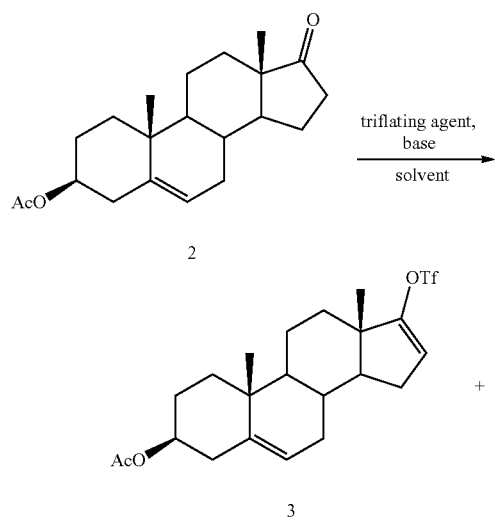

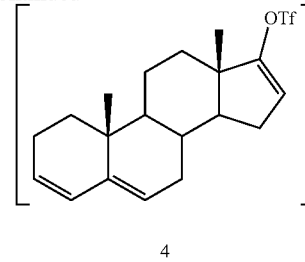

A series of bases was tested using dichloromethane as the solvent (Table 6). The % conversion and levels of the impurity 4 were measured by $^1$H NMR.

TABLE 6

Alternative bases for the formation of the triflate

| Triflating agent | Base | Solvent | Time | % conversion[2] | %4[2] |
|---|---|---|---|---|---|
| Tf$_2$O (1.0 eq.) | 2,6-lutidine (1.2 eq.) | DCM | 24 hrs | 60% | 0% |
| Tf$_2$O (1.1 eq.) | 2,6-lutidine (1.4 eq.) | DCM | 3 hrs | 25% | 0% |
| Tf$_2$O (1.1 eq.) | 2,6-lutidine (1.7 eq.) | DCM | 2.5 hrs | 13% | 0% |
| Tf$_2$O (1.1 eq.) | 2,6 lutidine (1.0 eq.) | DCM | 4.5 hrs[1] | 85% | 0% |
| Tf$_2$O (1.1 eq.) | Et$_3$N (1.4 eq.) | DCM | 3 hrs | 40% | 0% |
| Tf$_2$O (1.1 eq.) | Et$_3$N (1.7 eq.) | DCM | 2.5 hrs | 7% | 0% |
| Tf$_2$O (1.1 eq.) | Et$_3$N (1.0 eq.) | DCM | 1.5 hrs | 50% | 0% |
| Tf$_2$O (1.1 eq.) | Et$_3$N (1.0 eq.) | DCM | 4.5 hrs[1] | 77% | 0% |
| Tf$_2$O (1.1 eq.) | $^i$Pr$_2$EtN (1.0 eq.) | DCM | 4.5 hrs[1] | 80% | 0% |
| Comparative examples: | | | | | |
| Tf$_2$O (1.0 eq.) | 2,6-di-tert-butyl-4-methyl pyridine (1.2 eq.) | DCM | 16 hrs | 80% | Trace |
| Tf$_2$O (1.1 eq.) | 2,6-di-tert-butyl-4-methyl pyridine (1.4 eq.) | DCM | 3 hrs | 100% | 17% |

[1]Base added to a mixture of 2 and triflic anhydride.
[2]Conversion and % 4 determined by $^1$H NMR.

Repeating the reaction conditions reported in the prior art, using 2,6-di-tert-butyl-4-methylpyridine as the base, went to completion when 1.4 equivalents of base were used. However, 17% of the product was the eliminated impurity.

When the conditions were repeated using 2,6-lutidine and Et$_3$N as the base (1.4 eq.) the reactions proceeded to around 40% conversion with no evidence of the eliminated product 4.

It had been demonstrated that the reaction proceeded further with a higher equivalency of 2,6-di-tert-butyl-4-methylpyridine However, when 2,6-lutidine or Et$_3$N was used as the base, the reaction was inhibited. Therefore the amount of base was cut to 1 eq. and the conversion increased to 50% after 90 minutes.

This indicated that the reaction was inhibited by excess base, so the procedure was changed to a slow addition of the base (0.76 mmol. in 15 minutes) to a mixture of 2 and Tf$_2$O. The reaction reached around 80% conversion in 4.5 hours with Et$_3$N, 2,6-lutidine and $^i$Pr$_2$EtN.

When the addition time was extended to 3.5 hours the conversion remained around 80% with all the bases. However when the addition time was reduced to 2 minutes the reaction proceeded to only 45% conversion.

Step 2—The Suzuki Coupling

The Suzuki coupling was performed using reported methods. The product of the triflate formation was used in the Suzuki coupling unpurified.

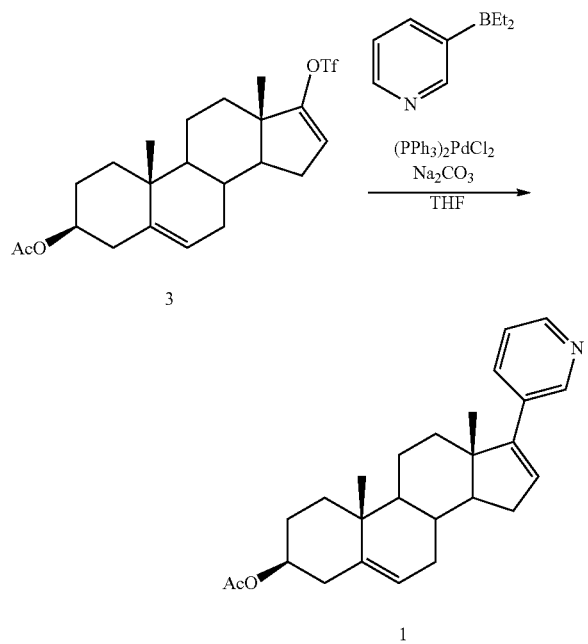

EXAMPLE 5

Further Investigations into Reaction Steps

As noted in Example 4, it has been noted that the formation of the triflate, 3, may depend on a number of factors:

1. The nature of the base used in the reaction;
2. The relative stoichiometries between the base and DHEA, 2;
3. The nature of the solvent used;
4. The reaction time.

Screen of Bases and Solvents for the Triflate Formation

A range of bases of varying basicity and character were used in the formation of triflate, 3. Reactions using each of these bases were performed in a variety of solvents. Dichloromethane, 1,2-dichloroethane and chloroform were investigated in order to expand the range of chlorinated solvents utilised for the triflate formation. Ethyl acetate, methyl tert-butyl ether and iso-hexane were studied in order to expand the nature of the solvents tested.

Each reaction was performed using 250 mg of DHEA, 2, in 20 volumes of the solvent. Trifluoromethanesulfonic anhydride (1.1 eq.) was added to the solution followed by the base (1.0 eq.) after 15 minutes. After 2 hours, a sample of each reaction was quenched into methanol and the reactions examined by LCMS.

Results are shown in Table 7.

TABLE 7

| | Alternative bases for the formation of the triflate | | | | | | |
|---|---|---|---|---|---|---|---|
| | pKa of conjugate acid | $CH_2Cl_2$ | 1,2-dichloroethane | $CHCl_3$ | EtOAc | MTBE | $i$-hexane |
| $Et_3N$ | 10.6 | ✓ (66) <5% elim. | ✓ (71) <5% elim. | ✓ (36) 9% elim. | ✓ (56) | X | ✓ (54) + decomp. |
| 2,6-lutidine | 6.75 | ✓ (70) 6% elim | ✓ (75) | ✓ (44) | ✓ (51) 10% elim. | X | X |
| pyridine | 5.21 | ✓ (80) + decomp 4% elim. | ✓ (78) + decomp | X | ✓ (52) + decomp 4% elim. | X | X |
| N,N-diethylaniline | 5.20 | X decomp | X decomp | X decomp | X decomp 6% elim. | X decomp | X decomp |
| DABCO | 8.82 | ✓ (29) 0% elim. | ✓ (44) | X | ✓ (57) + decomp 0% elim. | X | X |
| DBU | 12 | ✓ (54) 0% elim. | ✓ (70) | X | X | X | X |
| $KO^tBu$ | 17 | ✓ (61) | ✓ (63) | X | X | X | X |
| NaH | 36 | X | ✓ (73) + decomp | ✓ (67) | X | X | X |

✓ - triflate detected by HPLC (% conversion w.r.t. unreacted ketone).
X - no triflate detectable.

It should be noted that if a result notes that decomposition was occurring, a lot of unidentifiable peaks were present in the LCMS. The numbers quoted in the brackets were the conversion of DHEA, 2, to triflate, 3, not the overall yield of 3. A reaction which states a conversion to the triflate but decomposition also, would not give a good isolated yield under the conditions used. However the reaction may have given a better result if different conditions were attempted.

The table entries also show ("elim.") the amount of eliminated product, 5, present by NMR.

Bases whose conjugate acids have a relatively low $pK_a$ gave the worst results, with competing reactions causing complications. For instance the major product noted when N,N-diethylaniline was used was the de-acetylated product, 4. This was a significant product after extended reaction time when pyridine was used as the base.

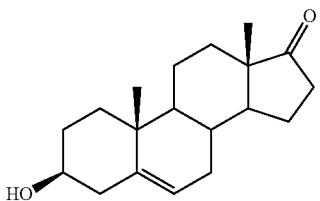

4

Reactions performed in ethers and hydrocarbons showed problems with solubility of the reactant along with their reactivity.

Chlorinated compounds proved to be the optimal family of solvents for use in this reaction. It was noted that on the whole, reactions in dichloromethane and 1,2-dichloroethane were comparable whereas those in chloroform were retarded to some degree.

The levels of the eliminated product, 5, could not be detected by LCMS. Therefore selected samples were concentrated and the $^1$H NMR of the residue was taken. These samples were selected due to their higher levels of impurities shown in the LCMS. The level of the eliminated product was not detected at over 10% levels in any of the reactions and was not detected at all when DABCO and DBU were used.

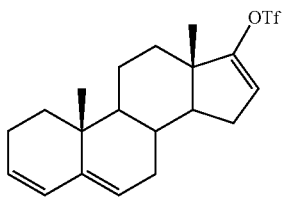

5

It should be noted that from the initial studies using 2,6-di-tert-butyl-4-methylpyridine ($pK_a$ 4.41 in 50% EtOH solvent at 27±2° C.) that if the reaction was halted before completion, the levels of the eliminated product, 5, were much reduced. Only when the equivalents of the base were increased did the level of elimination increase. The bases subsequently used above never drove the reaction to completion. If excess base were used the reaction stalled and if the reaction time was extended other competing side reactions decomposed the product to species other than 5.

Optimisation of the Reaction Profile of the Triflate Formation.

It had already been noted that the addition rate of the base to the reaction had a major effect on the yield of the reaction. In addition, the product decomposed if the reaction was left unquenched overnight. The effect of the relative timings of the addition of $Tf_2O$ and $Et_3N$, as well as the total reaction time, were explored.

Each reaction was performed on a 500 mg scale under standard conditions. Samples were taken at the prescribed times and partitioned between ethyl acetate and water. The organic layer was concentrated and the residue tested by $^1$H NMR.

Results are shown in Table 8. Any decomposition of the product was detected by the change in the shape of the aliphatic region of the spectra and could therefore only be qualitatively described.

TABLE 8 optimisation of the reaction profile of the triflate formation

| Time between $Tf_2O$ and $Et_3N$ addition (mins) | Time after $Tf_2O$ addition (mins) | % conversion | Decomposition? |
|---|---|---|---|
| 0.3 | 18 | 22 | None |
|  | 65 | 27 | None |
|  | 125 | 35 | None |
|  | 245 | 39 | None |
| 15 | 18 | 50 | None |
|  | 65 | 68 | Slight |
|  | 125 | 75 | Some |
|  | 245 | 75 | Significant |
| 60 | 18 | 21 | None |
|  | 65 | 71 | Slight |
|  | 125 | 75 | Significant |
|  | 245 | 75 | Significant |

The first point to note is that the formation of the triflate started to occur without the presence of the base, but addition of the bases increased the rate of reaction.

The results also indicated that the reaction was essentially complete 1 hour after the addition of the base. Extension of the reaction time beyond an hour resulted in a reduction in the quality of the triflate due to decomposition of the product.

Any decomposition occurring was not forming the eliminated product, 5, but other unidentified compounds.

Examination of the Optimum Relative Stoichiometry for the Triflate Formation

It had already been noted that the use of large excesses of base lead to poor conversion of DHEA, 2, to the triflate, 3, and that use of large excesses of $Tf_2O$ lead to rapid decomposition of the product. We wanted to investigate the effect of changing the relative stoichiometry of the two reactants across a narrow range.

Each reaction was performed using 250 mg of DHEA under standard conditions. Triethylamine was added 15 minutes after the addition of $Tf_2O$ and the reaction sampled after 2 hours. Results are shown in Table 9.

TABLE 9 optimum relative stoichiometry for the triflate formation

| Eq. $Tf_2O$ | Eq. $Et_3N$ | Conversion after 2 hours[1] |
|---|---|---|
| 0.8 | 0.8 | 33% |
| 1.1 | 0.8 | 66% |
| 1.4 | 0.8 | 81% + decomposition[2] |
| 0.8 | 1.1 | 36% |
| 1.1 | 1.1 | 64%[2] |
| 1.4 | 1.1 | 83% |
| 0.8 | 1.4 | 40%[2] |
| 1.1 | 1.4 | 53% |
| 1.4 | 1.4 | 70% |

[1]Measured by LCMS
[2]Conversion confirmed by $^1$H NMR.

These results confirmed that the number of equivalents of triflic anhydride needs to be higher than the number of equivalents of base for optimum conversion of DHEA to the triflate, 3. However, reducing the amount of base to sub-stoichiometric levels did not affect the conversion.

The invention claimed is:

1. In a process for the preparation of a compound of formula (I):

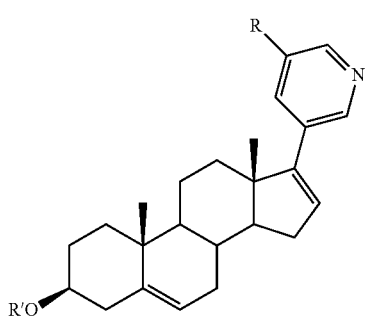

where R' represents hydrogen or a lower acyl group having 2 to 4 carbon atoms and R represents a hydrogen atom or an alkyl group of 1-4 carbon atoms; or a pharmaceutically acceptable salt thereof;

the improvement comprising the step of recovering a salt selected from the hydrochloride and the ditoluoyltartrate of the compound, where R' represents a lower acyl group having 2 to 4 carbon atoms and R is as defined above, from ethyl acetate.

2. A process as claimed in claim 1 in which the recovered salt of the compound of the formula (I) is further converted to the free base.

3. A process as claimed in claim 2 in which the free base is further converted to a pharmaceutically acceptable acid addition salt.

4. A process as claimed in claim 3 in which the pharmaceutically acceptable acid addition salt is selected from acetates, citrates, lactates, alkanesulfonates and optionally substituted tartrates.

5. A process as claimed in claim 2 in which the free base is Abiraterone acetate.

6. A process as claimed in claim 1 in which R is hydrogen and R' is an acetyl group.

* * * * *

UNITED STATES PATENT AND TRADEMARK OFFICE
CERTIFICATE OF CORRECTION

PATENT NO. : 8,338,588 B2
APPLICATION NO. : 13/317997
DATED : December 25, 2012
INVENTOR(S) : Hunt It is certified that error appears in the above-identified patent and that said Letters Patent is hereby corrected as shown below:

In the Specification

Column 4, line 39, please delete "lower acyloxy" and insert --lower acyl--.

Column 5, line 45, please delete "lower acyloxy" and insert --lower acyl--.

Signed and Sealed this
Ninth Day of July, 2013

Teresa Stanek Rea
*Acting Director of the United States Patent and Trademark Office*